United States Patent
Shin et al.

(10) Patent No.: US 7,212,694 B2
(45) Date of Patent: May 1, 2007

(54) FIBER-OPTIC SENSING SYSTEM FOR MEASURING CURVATURE

(76) Inventors: Chow-Shing Shin, National Taiwan University., No. 1, Sec. 4, Roosevelt Road, Taipei (TW) 106; Chun-Pin Lin, National Taiwan University., No. 1, Sec. 4, Roosevelt Road, Taipei (TW) 106; Uei-Ming Li, National Taiwan University., No. 1, Sec. 4, Roosevelt Road, Taipei (TW) 106

(*) Notice: Subject to any disclaimer, the term of this patent is extended or adjusted under 35 U.S.C. 154(b) by 0 days.

(21) Appl. No.: 11/248,369

(22) Filed: Oct. 12, 2005

(65) Prior Publication Data
US 2006/0140531 A1 Jun. 29, 2006

(30) Foreign Application Priority Data
Dec. 27, 2004 (TW) .............................. 93140791 A

(51) Int. Cl.
*G02B 6/00* (2006.01)
*G02B 6/26* (2006.01)
*G02B 6/42* (2006.01)
*G02B 6/06* (2006.01)
*A61B 1/00* (2006.01)

(52) U.S. Cl. .......................... 385/12; 385/13; 385/32; 385/117; 600/145

(58) Field of Classification Search ................ 385/12, 385/13, 32; 600/587, 590
See application file for complete search history.

(56) References Cited

U.S. PATENT DOCUMENTS

| 5,503,559 A | * | 4/1996 | Vari ............................ 433/224 |
| 7,065,284 B2 | * | 6/2006 | Ao et al. .................... 385/140 |
| 2005/0137657 A1 | * | 6/2005 | Dykaar ....................... 607/88 |

FOREIGN PATENT DOCUMENTS

| JP | 10112520 | * | 11/1999 |
| JP | 2003-102677 | * | 8/2003 |
| JP | 2004-345545 | * | 9/2004 |

* cited by examiner

*Primary Examiner*—Frank G. Font
*Assistant Examiner*—Charlie Peng
(74) *Attorney, Agent, or Firm*—Law Offices of John Chupa & Associates, P.C.

(57) ABSTRACT

The invention provides a fiber-optic sensing system for measuring a curvature in a small and elongated cavity of an object. The system includes a light source, an optical fiber and a light signal reflecting device disposed at a distal end of the optical fiber. The optical source emits a light signal into the optical fiber. The distal section of the optical fiber is inserted into the cavity of the object which curvature is to be measured. The curvature of the cavity bends the distal section of the optical fiber so that attenuation of light signal transmitting through the distal section occurs. This attenuated signal is reflected by a reflecting device and coupled into a measuring device. Thereby the curvature is deduced in accordance with the amount of energy attenuation in the reflected light signal.

21 Claims, 5 Drawing Sheets

FIBER-OPTIC SENSING SYSTEM FOR MEASURING CURVATURE

BACKGROUND OF THE INVENTION

1. Field of the Invention

This invention relates to a fiber-optic sensing system for measuring the curvature, especially for measuring the curvature of an elongated cavity of an object.

2. Description of the Prior Art

Curvature measurement is important in some fields but hard to perform. For example, in root canal treatment, the measurement of root canal curvature is very useful but complicated to make.

Root canal treatment involves the removal of diseased canal tissue and affected canal wall with super-elastic Ni—Ti rotary file. Due to the curvature of root canals, the rotary files are under rotating bending condition at work, which incurs an alternate tension and compression in the files. Such an alternating loading will lead to fatigue failure. Fracture of rotary file inside the canal is highly undesirable as it is difficult to take the fractured part out. It is therefore useful if one can predict the remaining life of a rotary file. To achieve this purpose, it is important to know the degree of curvature of the root canal.

Conventional method to measure the curvature of root canal employs X-ray radiography. Owing to the three dimensional nature of the canal, more than one radiograph from different directions are needed to obtain a realistic picture of the curvature. However, obstruction form other teeth may interfere with the image. Furthermore, X-ray radiography involves expensive equipment and radiation hazard.

Accordingly, an objective of the invention is to provide a fiber-optic sensing system for measuring curvature, especially for measuring the curvature of a small and elongated cavity such as root canal. This technique for measuring the curvature of the root canal is not only cheaper and more expedient than the conventional X-ray technique, but also it involves no radiation hazard.

SUMMARY OF THE INVENTION

An objective of the invention is to provide a fiber-optic sensing system for measuring curvature. The invention provides a low-cost, radiation free, easy-to-use and reliable fiber-optic sensing system for measuring curvature. The invention employs the principle that an optical fiber will dissipate light energy to different degrees if it is bent to different curvature. The accuracy of the fiber-optic sensing system of the invention is not affected by the bending and the vibration of the conducting optical fiber and the fluctuation in the light source intensity.

According to a first preferred embodiment of the invention, the fiber-optic sensing system is for measuring the curvature of a one-end-opened and elongated cavity of an object. The system consists of a light source, a coupler, an optical fiber, a first light signal reflecting device and a signal processing device. Light signal emitted by the light source is coupled by the coupler into the optical fiber. The distal section of the optical fiber is inserted into the cavity of the object to be measured such that this distal section of the optical fiber is bent and attenuates the light signal transmitted through it. The first light signal reflecting device disposed at a distal end of the optical fiber is for reflecting the attenuated light signal. The signal processing device receives the attenuated reflected light signal through the coupler and measures the energy, thereby deduce the curvature in accordance with the amount of energy attenuation.

According to a second preferred embodiment of the invention, the fiber-optic sensing system is for measuring the curvature of a one-end-opened and elongated cavity in an object. The system includes a light source, a coupler, a sensing optical fiber, a reference optical fiber, a first light signal reflecting device, a second light signal reflecting device and a signal processing device. The light signal emitted by the light source is coupled into a sensing fiber and a reference optical fibers by the coupler. The distal section of the sensing optical fiber is inserted into the cavity of the object to be measured, such that the distal section of the sensing optical fiber is bent and the light signal transmitted through it is attenuated. The reference optical fiber is bundled together with the sensing optical fiber up to the point where the sensing fiber is inserted into the cavity of the object. The first light signal reflecting device disposed at a distal end of the sensing optical fiber is for reflecting the attenuated light signal. The second light signal reflecting device disposed at the distal end of the reference optical fiber is for reflecting the part of light signal emitted by the light source as a reference. The signal processing device, coupled to the sensing and reference fibers through the coupler, is for receiving and measuring the energy of the attenuated and reflected light signal and the reference signal, and calculating the curvature in accordance with the energy of the attenuated and reflected light signal and the energy of the reference signal.

The foregoing aspects and many of the advantages of this invention will become more readily appreciated and better understood by reference to the following detailed description, when taken in conjunction with the accompanying drawings.

BRIEF DESCRIPTION OF THE APPENDED DRAWINGS

DETAILED DESCRIPTION OF THE INVENTION

An objective of the invention is to provide a fiber-optic sensing system for measuring curvature. The invention employs the principle that an optical fiber will dissipate different amount of light energy according to the degree of curvature it is bent. A description will now be given of the preferred embodiments of the invention with reference to the drawings for showing the principle and the characteristics of the invention. It should however be recognized that the present invention can be practiced in a wide range of other embodiments besides those explicitly described, and the scope of the present invention is expressly not limited except as specified in the accompanying claims.

The components of the different elements are not shown to scale. Some dimensions of the related components are exaggerated and meaningless portions are not drawn to provide a clearer description and easier comprehension of the present invention.

Figure 1A:
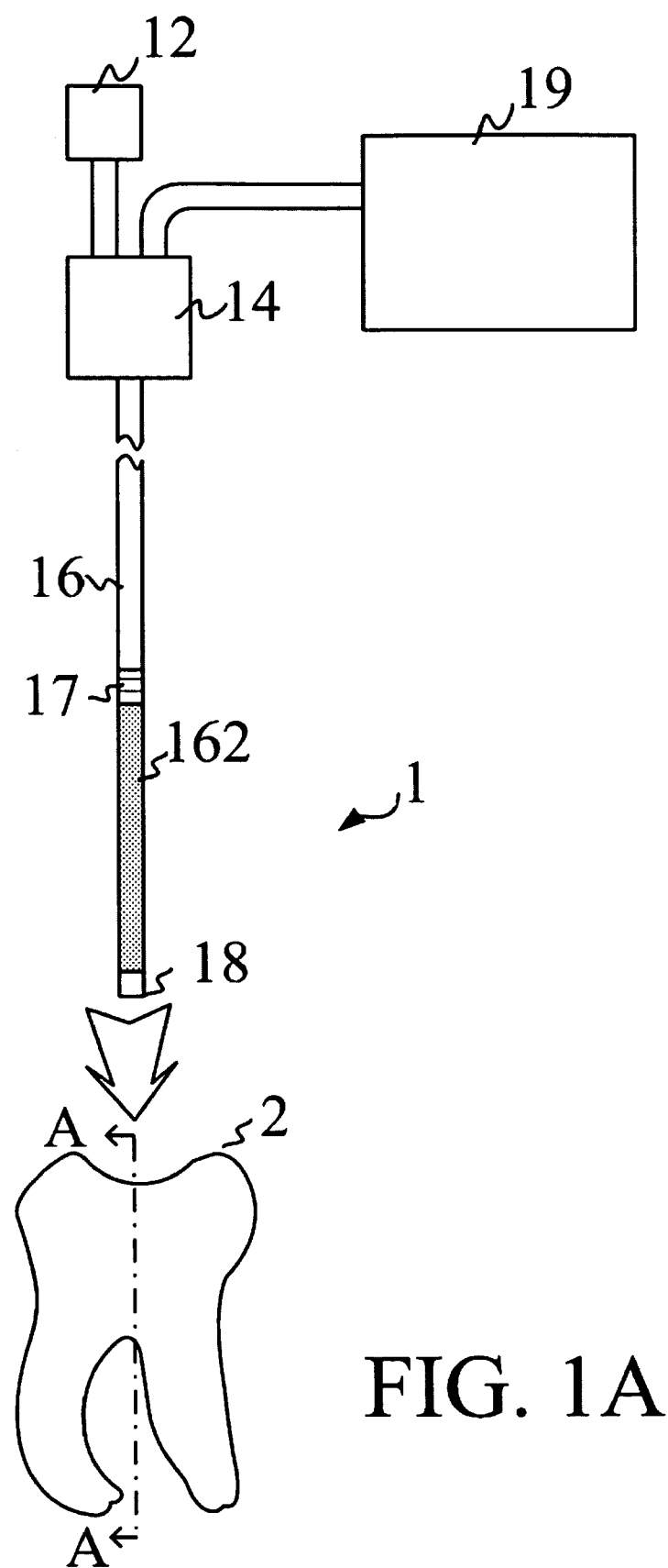
FIG. 1A is a schematic view of the fiber-optic curvature measuring system according to the first preferred embodiment of the invention, and the figure also shows the measured object (tooth) for the fiber-optic curvature measuring system.
Figure 1B:
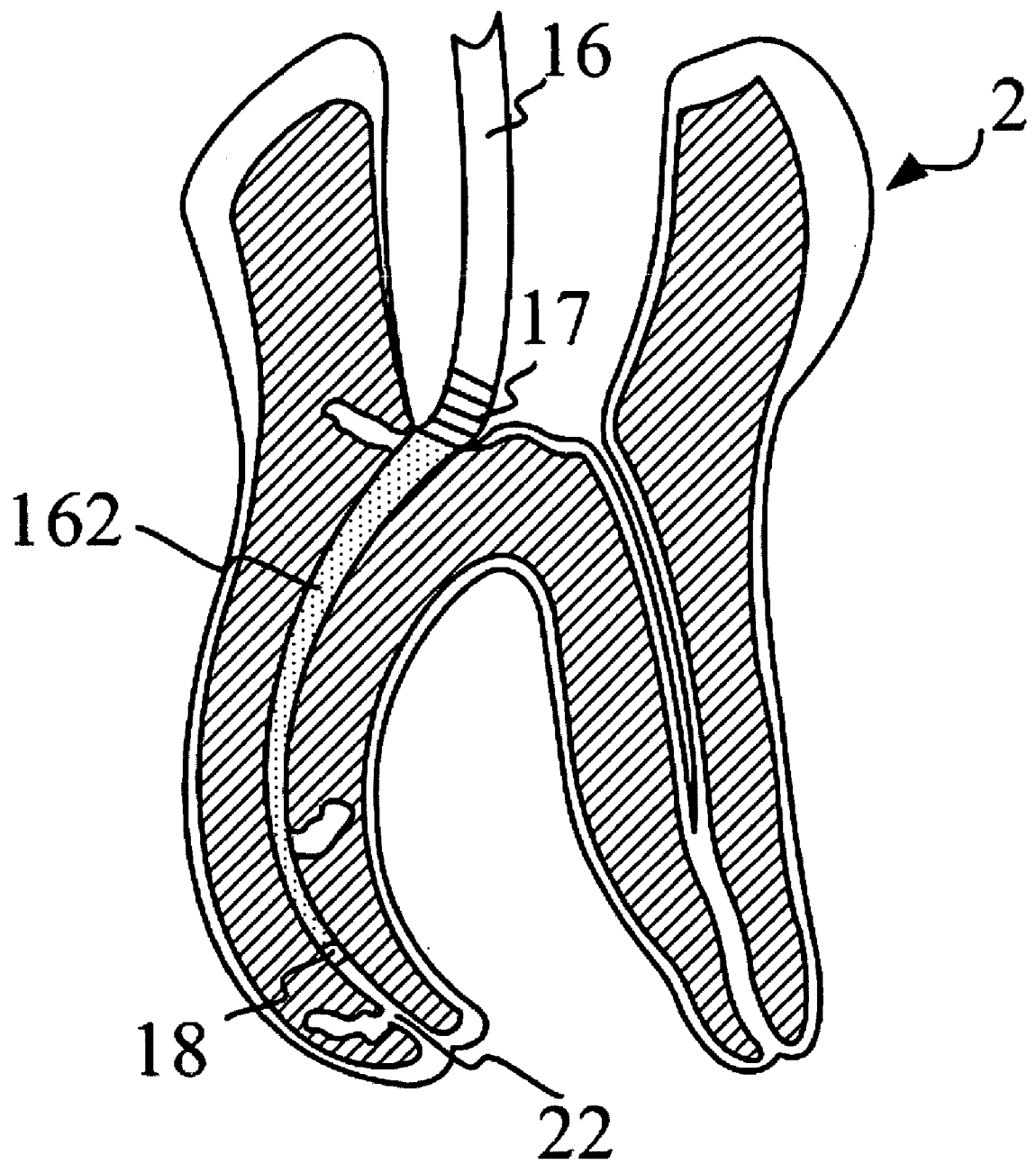
FIG. 1B shows that the optical fiber 16 in FIG. 1A is inserted via the distal section thereof into the root canal of the tooth, this figure also shows a cross-sectional view of the tooth in FIG. 1A along the A—A line to display the root canal.

Referring to FIG. 1A and FIG. 1B, the fiber-optic curvature measuring system 1 according to the first preferred embodiment of the invention is disclosed. FIG. 1A and FIG. 1B also show the measured object (tooth) 2 for the fiber-optic curvature measuring system 1.

As shown in FIG. 1A, according to the first preferred embodiment of the invention, the fiber-optic curvature measuring system 1 includes a light source 12, a coupler 14, an optical fiber 16, a first light signal reflecting device 18 and a signal processing device 19.

Light emitted by the light source 12 is coupled into the optical fiber 16 through the coupler 14.

Particularly, as shown in FIG. 1B, the optical fiber 16 is inserted via a distal section 162 thereof into the cavity (root canal) 22 of the object (tooth) 2 such that the distal section 162 of the optical fiber is bent to attenuate the light signal transmitted over the distal section 162. The first light signal reflecting device 18 disposed at a distal end of the optical fiber 16 is for reflecting the attenuated light signal. The signal processing device 19, is for receiving the attenuated and reflected light signal through the coupler 14, measuring its energy, and calculating the curvature in accordance with the energy of the attenuated and reflected light signal.

In this first preferred embodiment, a fiber Bragg grating or a metallic film coated on the distal end of the optical fiber 16 can be employed as the first light signal reflecting device 18. The former has a high reflectivity for some particular optical wavelength, but the grating needs to occupy at least 1 mm of the distal section of the optical fiber. The latter has a lower reflectivity, but the reflected spectrum is wider, and it only has a thickness of several micrometers.

Figure 2:
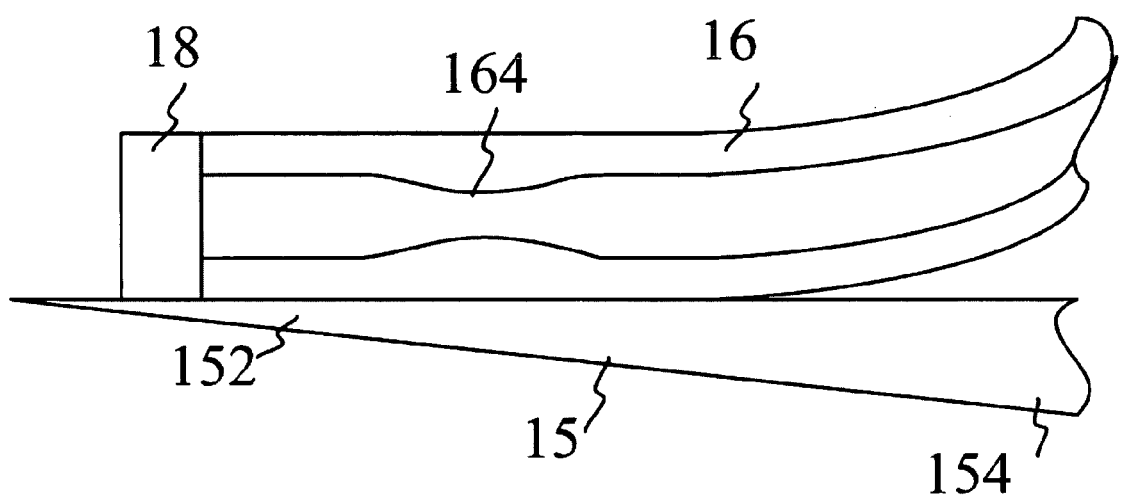
FIG. 2 shows a protective base and the distal end of the optical fiber having at least one necked segment in the fiber core in an embodiment.

FIG. 2 shows a protective base 15 and the distal end of the optical fiber 16 having at least one necked segment 164 in the fiber core in an embodiment.

In the embodiment shown in FIG. 2, the core of the optical fiber 16 in the fiber-optic curvature measuring system 1 includes at least one necked segment 164 disposed within the distal section 162. The necked segment 164 is capable of intensifying the attenuation of the light signal transmitted over the distal section 162 under bending, thereby increasing the sensitivity of the measurement.

Referring to FIG. 2, the fiber-optic curvature measuring system 1 further includes a protective base 15. The protective base 15 is made of an elastic material. It includes an insertion portion 152, onto which the distal section 162 of the optical fiber is attached, and a handheld portion 154. The insertion portion 152 is adapted to be inserted together with the distal section 162 into the root canal 22 of tooth 2, thus lowering the possibility of optical fiber fracture inside the root canal. If the protective base has a suitable groove for accommodating the optical fiber, the protection of the optical fiber would be even better.

Since the measurement is based on light energy reflected from the sensor, accuracy will be affected by other sources of light energy variation. Light energy variation in the optical fiber may be brought about by bending and vibration of the portion of the optical fiber beyond the sensor, and the fluctuation of the light source. To alleviate these effects, a reference optical fiber 31 bundled together with the sensing fiber is included in the second preferred embodiment of the invention to provide a reference signal.

Figure 3:
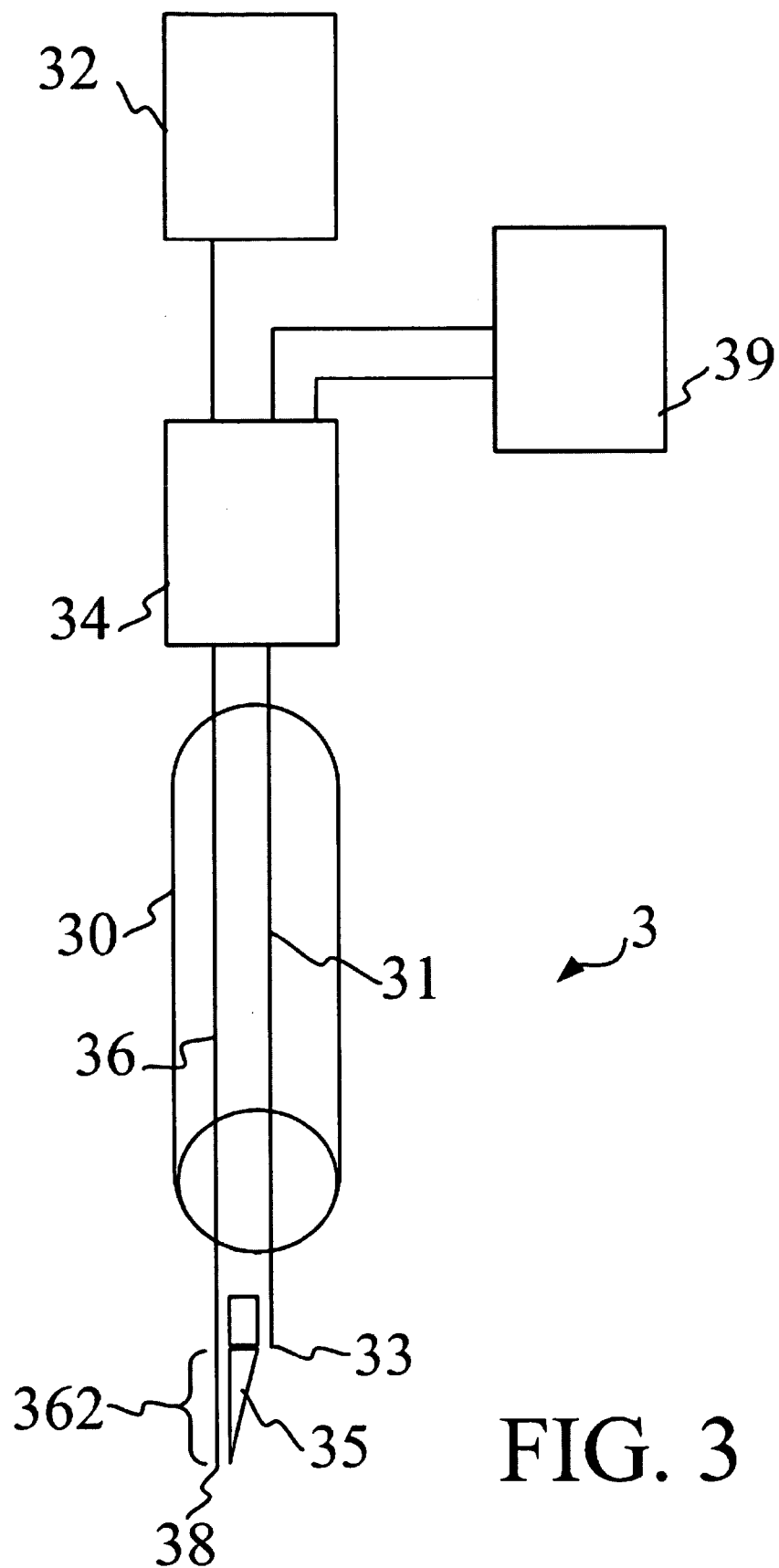
FIG. 3 is a schematic view of the fiber-optic curvature measuring system according to the second preferred embodiment of the invention. In this preferred embodiment, a second optical fiber is added to provide a reference standard.

FIG. 3 shows the schematic view of the fiber-optic curvature measuring system 3 according to the second preferred embodiment of the invention. It includes a light source 32, a coupler 34, a sensing optical fiber 36, a reference optical fiber 31, a first light signal reflecting device 38, a second light signal reflecting device 33 and a signal processing device 39. The lead wire sections of these two optical fibers are bundled together to ensure both of the fibers run the same route and receive the same disturbances.

Light emitted by the light source 32 is coupled by the coupler 34 into a sensing optical fiber 36 and a reference optical fiber 31. The distal section 362 of the sensing optical fiber 31 is inserted into the cavity of the object to be measured (not shown) and is bent and attenuates the light signal transmitted over the distal section 362. The reference optical fiber 31 sees all the bending, vibration and light source fluctuation as that of the sensing optical fiber 36 except for the attenuation inside the cavity. Thus light intensity variations outside the sensor are proportionately affected in both the sensing and reference fibers. The signal reflected from the first light signal reflecting device 38 disposed at a distal end of the sensing optical fiber 36 is designated $P_{sig}$ and the signal reflected from a second light signal reflecting device 33 disposed at a distal end of the reference optical fiber 31 is designated $P_{ref}$. The normalized value $P_{sig}/P_{ref}$ will be free from external perturbations that cause variation in light energy except that from the curvature sensor. In this second preferred embodiment, either a fiber Bragg grating or a metallic film coated on the distal end of the optical fiber can be employed as the first light signal reflecting device 38 and a second light signal reflecting device 33. The protective base 35 shown in FIG. 3 is the same as that in the embodiment shown in FIG. 2.

A third embodiment evolving from the second preferred embodiment is illustrated in FIGS. 1A and 1B. This embodiment adds a second light signal reflecting device 17 upstream of the distal section 162 in the optical fiber 16 of the fiber-optic curvature measuring system 1. This second light signal reflecting device 17 is wavelength selective and reflects part of the light energy emitted by the light source 12 to provide a reference signal. In this way, a reference signal can be obtained by using only one optical fiber for improving the accuracy. In this embodiment, the second light signal reflecting device 17 is a fiber Bragg grating.

Figure 4:
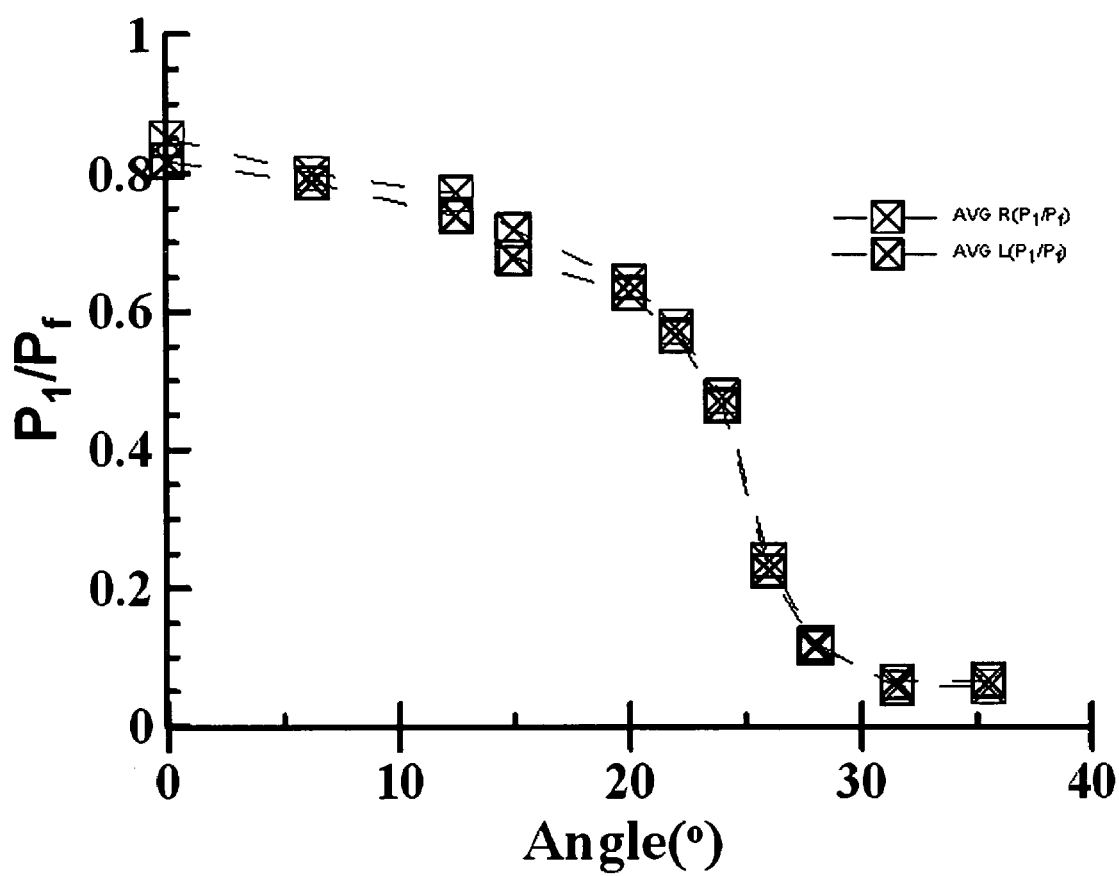
FIG. 4 shows the measurement results for different Schneider's angles using the embodiment of the fiber-optic curvature measuring system in FIG. 3.

The relation between the attenuation of the light energy and the curvature can be evaluated by calibration in advance. FIG. 4 is the result of such calibration using the fiber-optic curvature measuring system 3 in FIG. 3. The curvature of the root canal is usually expressed by Schneider's angle. FIG. 4 shows the normalized reflected energy measured under different Schneider's angles. The two curves are the results of the optical fiber curvature sensor bent respectively to the right and to the left. The energy variation of the light source is substantially changed and the lead wire portion of the optical fiber is shaken and bent during the measurement process, but the value $P_{sig}/P_{ref}$ is not affected. Bending either ways showed good reproducibility.

To sum up, the description of the above-mentioned preferred embodiments is for providing a better understanding on the strengths and principles of the present invention, not for limiting the domain of the invention. Moreover, it aims to include various modifications and arrangements parallel in form into the domain of the patent applied by this present invention. Due to the above mentioned, the domain of the patent applied by the invention should be explained in a macro view to cover all kinds of possible modifications and arrangements of equal form.

What is claimed is:

1. A fiber-optic sensing system for measuring a curvature in an elongated root canal of a tooth, said system comprising:
   a light source for emitting a light signal;
   a coupler, for coupling the light signal emitted by the light source into an optical fiber;
   the optical fiber, receiving light from the light source via the coupler, the distal section of the fiber being inserted into the root canal of the tooth which curvature is to be measured;
   a first light signal reflecting device, disposed at a distal end of the optical fiber, for reflecting the attenuated light signal; and
   a signal processing device, for measuring the attenuated reflected light signal through the coupler, and calculating the curvature in accordance with the energy of the attenuated reflected light signal.

2. The fiber-optic sensing system of claim 1, wherein a core of the optical fiber comprises at least one necked segment disposed within the distal section, the necked segment is capable of intensifying the attenuation of the light signal transmitted over the distal section under bending.

3. The fiber-optic sensing system of claim 1, further comprising a protective base made from an elastic material, the protective base comprising an insertion portion, onto which the distal section of the optical fiber is attached, and a handheld portion, the insertion portion being adapted to be inserted together with the distal section into the root canal of the tooth, the handheld portion being positioned outside the root canal of the tooth when the insertion portion is inserted into the root canal of the tooth.

4. The fiber-optic sensing system of claim 1, further comprising a second light signal reflecting device, disposed in the optical fiber at the upstream of the distal section, for reflecting selected part of the light signal emitted by the light source to provide a reference signal, wherein the signal processing device also receives and measures the reference signal through the coupler, and calculates the curvature in accordance with the energy of the attenuated and reflected light signal and the energy of the reference signal.

5. The fiber-optic sensing system of claim 4, wherein the first light signal reflecting device and the second light signal reflecting device are fiber Bragg gratings, respectively.

6. The fiber-optic sensing system of claim 4, wherein the first light signal reflecting device is a metallic film coated on the distal end of the optical fiber, and the second light signal reflecting device is a fiber Bragg grating.

7. A fiber-optic sensing system for measuring a curvature in an elongated cavity of an object, said system comprising:
   a light source for emitting a light signal;
   a coupler, for coupling the light signal emitted by the light source into a sensing optical fiber and a reference optical fiber;
   the sensing optical fiber, the distal section of the sensing optical fiber is inserted into the cavity of the object which curvature is to be measured;
   the reference optical fiber, being bundled with the sensing optical fiber, wherein when the distal section of the sensing optical fiber is inserted into the cavity of the object and suffer a bending thereof, the reference optical fiber is not inserted into the cavity of the object;
   a first light signal reflecting device, disposed at a distal end of the sensing optical fiber, for reflecting the attenuated light signal;
   a second light signal reflecting device, disposed at a distal end of the reference optical fiber for reflecting the light signal emitted by the light source as a reference signal; and
   a signal processing device, for measuring the attenuated reflected light signal and the reference signal through the coupler, and calculating the curvature in accordance with the energy of the attenuated and reflected light signal normalized with the energy of the reference signal.

8. The fiber-optic sensing system of claim 7, wherein the reference optical fiber is shorter than the sensing optical fiber.

9. The fiber-optic sensing system of claim 8, wherein a difference between the length of the reference optical fiber and the length of the sensing optical fiber is equal to the length of the distal section of the sensing optical fiber.

10. The fiber-optic sensing system of claim 7, wherein a core of the sensing optical fiber comprises at least one necked segment disposed within the distal section, the at least one necked segment capable of intensifying the attenuation of the light signal transmitted over the distal section under bending.

11. The fiber-optic sensing system of claim 7, further comprising a protective base made from an elastic material, the protective base comprising an insertion portion, onto which the distal section of the optical fiber is attached, and a handheld portion, the insertion portion being adapted to be inserted together with the distal section into the cavity of object, the handheld portion being positioned outside the cavity of the object when the insertion portion is inserted into the cavity of the object.

12. The fiber-optic sensing system of claim 7, wherein the first light signal reflecting device and the second light signal reflecting device are both fiber Bragg gratings.

13. The fiber-optic sensing system of claim 7, wherein the first light signal reflecting device is a metallic film coated on the distal end of the sensing optical fiber, and the second light signal reflecting device is a fiber Bragg grating.

14. The fiber-optic sensing system of claim 7, wherein the first light signal reflecting device is a fiber Bragg grating, and the second light signal reflecting device is a metallic film coated on the distal end of the reference optical fiber.

15. The fiber-optic sensing system of claim 7, wherein the first light signal reflecting device is a first metallic film coated on the distal end of the sensing optical fiber, and the second light signal reflecting device is a second metallic film coated on the distal end of the reference optical fiber.

16. The fiber-optic sensing system of claim 7, wherein the object is a tooth, and the cavity is a root canal of the tooth.

17. A fiber-optic sensing system for measuring a curvature in an elongated cavity of an object, said system comprising:
   a light source for emitting a light signal;
   a coupler, for coupling the light signal emitted by the light source into an optical fiber;
   the optical fiber, receiving light from the light source via the coupler, the distal section of the fiber being inserted into the cavity of the object which curvature is to be measured;

a first light signal reflecting device, disposed at a distal end of the optical fiber, for reflecting the attenuated light signal;

a signal processing device, for measuring the attenuated reflected light signal through the coupler, and calculating the curvature in accordance with the energy of the attenuated reflected light signal; and a second light signal reflecting device, disposed in the optical fiber at the upstream of the distal section, for reflecting selected part of the light signal emitted by the light source to provide a reference signal;

wherein the signal processing device also receives and measures the reference signal through the coupler, and calculates the curvature in accordance with the energy of the attenuated and reflected light signal and the energy of the reference signal.

18. The fiber-optic sensing system of claim 17, wherein a core of the optical fiber comprises at least one necked segment disposed within the distal section, the necked segment is capable of intensifying the attenuation of the light signal transmitted over the distal section under bending.

19. The fiber-optic sensing system of claim 17, further comprising a protective base made from an elastic material, the protective base comprising an insertion portion, onto which the distal section of the optical fiber is attached, and a handheld portion, the insertion portion being adapted to be inserted together with the distal section into the cavity of object, the handheld portion being positioned outside the cavity of the object when the insertion portion is inserted into the cavity of the object.

20. The fiber-optic sensing system of claim 17, wherein the first light signal reflecting device and the second light signal reflecting device are fiber Bragg gratings, respectively.

21. The fiber-optic sensing system of claim 17, wherein the first light signal reflecting device is a metallic film coated on the distal end of the optical fiber, and the second light signal reflecting device is a fiber Bragg grating.

* * * * *